United States Patent [19]

Goetz et al.

[11] Patent Number: 4,629,799
[45] Date of Patent: Dec. 16, 1986

[54] PREPARATION OF 3-FORMYLTETRAHYDROTHIOPYRANS

[75] Inventors: Norbert Goetz, Worms; Dieter Jahn, Edingen-Neckarhausen; Gernot Reissenweber, Boehl-Iggelheim; Heinz Eckhardt, Ludwigshafen, all of Fed. Rep. of Germany

[73] Assignee: BASF Aktiengesellschaft, Ludwigshafen, Fed. Rep. of Germany

[21] Appl. No.: 648,877

[22] Filed: Sep. 10, 1984

[30] Foreign Application Priority Data

Sep. 17, 1983 [DE] Fed. Rep. of Germany ....... 3333678

[51] Int. Cl.$^4$ .......................................... C07D 335/02
[52] U.S. Cl. ..................................................... 549/13
[58] Field of Search ........................................ 549/13

[56] References Cited

U.S. PATENT DOCUMENTS 3,733,336  5/1973  Wagner et al. ...................... 549/13
4,273,945  6/1981  Heilen et al. ......................... 549/13
4,422,864  12/1983 Becker et al. ........................ 549/13

FOREIGN PATENT DOCUMENTS 1479916  7/1977  European Pat. Off. ............. 549/13
0071707  2/1983  European Pat. Off. ............. 549/13

OTHER PUBLICATIONS

Morrison et al, textbook, "Organic Chemistry", Allyn and Bacon, Inc., Boston, 1973, pp. 289–293.
House, Modern Synthetic Reactions, 1972, p. 15.
Annalen der Chemie, vol. 660, Table 1, pp. 17–19.
March; Jerry, textbook, "Advanced Organic Chemistry", McGraw Hill, N.Y., N.Y., 1977, pp. 707–711.
Chemical Abstracts, vol. 87, No. 3, 1977, p. 23096w.
J. M. McIntosh and Hamdy Khalil, Phase-Transfer Catalyzed Syntheses . . . , J. Org. Chem., vol. 42, No. 12, 1977, pp. 2123–2126.
Z. Lebensm. Unters. Forsch., 170 (1980), 34–35.
J. Chem. Soc. (1958) pp. 2888–2890.
Rylander, Catalytic Hydrogenation over Platinum Metals, Academic Press, New York, 1967, pp. 107–108.
H. D. Hartough, Thiophene and Its Derivatives, Interscience Publishers, New York, 1952, pp. 167–168.
Angew. Makromol. Chem. 52 (1976), 63–70.
Friefelder, Practical Catalytic Hydrogenation (Wiley Interscience, New York, 1971, pp. 153–154.

Primary Examiner—Henry R. Jiles
Assistant Examiner—J. G. Mullins
Attorney, Agent, or Firm—John H. Shurtleff

[57] ABSTRACT

3-Formyltetrahydrothiopyrans are prepared by hydrogenating a 3-formyl-5,6-dihydro-2H-thiopyran in the presence of a catalyst containing nickel, cobalt, platinum, copper and/or silver; if necessary, the 3-formyl-5,6-dihydro-2H-thiopyrans are prepared by converting bis-($\beta$-formylethyl) sulfides and/or 3-formyl-4-hydroxytetrahydrothiopyrans in the presence of an acidic catalyst, and, if required, these bis-($\beta$-formylethyl) sulfides and/or 3-formyl-4-hydroxytetrahydrothiopyrans are prepared by reacting an acrolein with hydrogen sulfide (a) in the presence of a basic catalyst and of methylene chloride, aromatic hydrocarbons and/or 1,1,2-trichloroethane as solvents, and/or (b) in the presence of a carboxamide.

The compounds obtainable by the process according to the invention are useful starting materials for the preparation of dyes, drugs and pesticides.

20 Claims, No Drawings

PREPARATION OF 3-FORMYLTETRAHYDROTHIOPYRANS

The present invention relates to a process for the preparation of 3-formyltetrahydrothiopyrans by hydrogenation of a 3-formyl-5,6-dihydro-2H-thiopyran in the presence of a catalyst containing nickel, cobalt, platinum, copper and/or silver; if necessary, 3-formyl-5,6-dihydro-2H-thiopyrans are prepared by converting bis-($\beta$-formylethyl)sulfides and/or 3-formyl-4-hydroxytetrahydrothiopyrans in the presence of an acidic catalyst, and, if required, these sulfides and/or 3-formyl-4-hydroxytetrahydrothiopyrans are prepared by reacting an acrolein with hydrogen sulfide (a) in the presence of a basic catalyst and of methylene chloride, an aromatic hydrocarbon and/or 1,1,2-trichloroethane as solvents and/or (b) in the presence of a carboxamide.

It has been disclosed that 3-formyl-5,6-dihydro-2H-thiopyran can be prepared from acrolein and hydrogen sulfide in the presence of copper turnings and triethylamine at $-10°$ C. (Z. Lebensm. Unters. Forsch. 170 (1980), 34–35). German Published Application DAS 1,919,504 likewise describes a 2-stage preparation, ie. a reaction in the presence of a base and a solvent at from $-10°$ to $+150°$ C., followed by reaction of the product with a strong acid at from 60° to 160° C. The Examples illustrate a procedure which is carried out under superatmospheric pressure and in which the solvents used are chloroform and methanol, the bases used are tertiary amines and the acids used are phosphoric acid and sulfuric acid.

To date, the preparation of the saturated aldehyde 3-formyltetrahydrothiopyran has been described only in British Pat. No. 1,479,916. 3-Chloropropionaldehyde diethyl acetal and sodium hydrogen sulfide were first converted to 3-formyl-5,6-dihydro-2H-thiopyran, which was then hydrogenated over a palladium catalyst on a carbon carrier to give the saturated aldehyde. The Examples show that large amounts of catalyst are required; 1.5 g of catalyst comprising 10% of palladium on carbon were employed for 3.2 g of 3-formyl-5,6-dihydro-2H-thiopyran.

The conversion of unsaturated sulfides to saturated ones by hydrogenation over a palladium/charcoal catalyst is known. It should be pointed out that hydrogenation over heavy metal catalysts under the conventional conditions, ie. at elevated temperatures and under superatmospheric pressure, results in substantial hydrogenolysis (J. Chem. Soc. (1958), pages 2888–2890).

Furthermore, it has been stated that palladium catalysts are preferably used for the partial hydrogenation of $\alpha,\beta$-unsaturated aldehydes to the saturated aldehydes (Rylander, Catalytic Hydrogenation over Platinum Metals, Academic Press, New York, 1967, pages 107–108). German Laid-Open Application DOS 2,832,699 describes catalysts which consist of palladium and compounds of a rare earth metal, and points out that, when this combination is used, perhydrogenation of olefinically unsaturated aldehydes to the corresponding saturated alcohols is avoided, in spite of the sensitive aldehyde group. The literature points out that, although platinum catalysts are also suitable in the case of unsaturated aliphatic aldehydes, palladium is the catalyst of choice in every case, since only such catalysts selectively reduce the olefin group without effecting a substantial reduction of the carbonyl group. This is illustrated, by way of example, by the reduction of citronellal, in which palladium catalysts attack the olefinic double bond, but nickel catalysts attack the carbonyl group.

Nickel catalysts are rapidly poisoned by sulfo compounds, for example thiophene (H. D. Hartough, Thiophene and its Derivatives, Interscience Publishers, New York, 1952, pages 167–168). It should be pointed out that nickel catalysts and cobalt catalysts are used for the desulfurization of organic compounds, hydrogen sulfide being formed. Platinum catalysts are also poisoned by thiophene. Both thiophene compounds and thiolane compounds can undergo cleavage in the hydrogenation with copper, platinum and nickel catalysts. Furthermore, an article in Angew. Makromol. Chem. 52 (1976), 63–70 shows that nickel catalysts are effective desulfurization catalysts. Freifelder, Practical Catalytic Hydrogenation (Wiley Interscience, New York, 1971), pages 153–154 has also recommended palladium catalysts for the hydrogenation of unsaturated aldehdyes, and shows that platinum and nickel catalysts are unsuitable, and that nickel catalysts promote perhydrogenation.

German Published Application DAS 1,919,504 describes the preparation of 3-formyltetrahydrothiopyran (1-thiacyclo-$\Delta^3$-hexen-3-al) by reacting acrolein and hydrogen sulfide in the presence of an organic base and in the presence or absence of an organic solvent, and then subjecting the reaction product to after-treatment with a strong acid. The Examples state that the pressures used are as high as 6.5 atm gage pressure, the solvent is methanol or chloroform, and tertiary amines are used as bases; the hydrogen sulfide and the base are always taken initially, and the acrolein is then added to the mixture.

We have found that 3-formyltetrahydrothiopyrans of the formula

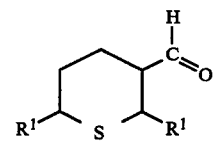   I where the individual radicals $R^1$ are each hydrogen or an aliphatic radical, are advantageously obtained by hydrogenation of a 3-formyl-5,6-dihydro-2H-thiopyran in the presence of a catalyst, if a 3-formyl-5,6-dihydro-2H-thiopyran of the formula

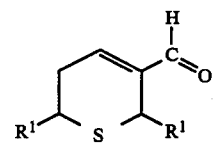   II where $R^1$ has the above meanings, is hydrogenated in the presence of a catalyst containing nickel, cobalt, platinum, copper and/or silver.

We have furthermore found that the process can be advantageously carried out if, in a first stage, a bis-(-formylethyl)sulfide of the formula

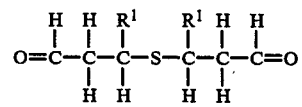   III where $R^1$ has the above meanings, and/or a 3-formyl-4-hydroxytetrahydrothiopyran of the formula

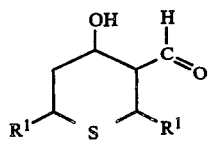　IV where $R^1$ has the above meanings, are converted in the presence of an acidic catalyst, and then, in a second stage, the resulting 3-formyl-5,6-dihydro-2H-thiopyran of the formula

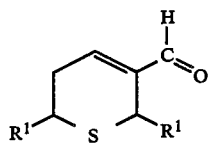　II where $R^1$ has the above meanings, is hydrogenated in the presence of a catalyst containing nickel, cobalt, platinum, copper and/or silver.

We have furthermore found that the process can advantageously be carried out if, in a first stage, an acrolein of the formula

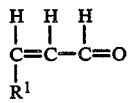　V where $R^1$ has the above meanings, is reacted with hydrogen sulfide (a) in the presence of a basic catalyst and of methylene chloride, an aromatic hydrocarbon and/or 1,1,2-trichloroethane as the solvent and/or (b) in the presence of a carboxamide, and then, in a second stage, the resulting mixture of a bis-(β-formylethyl)sulfide of the formula

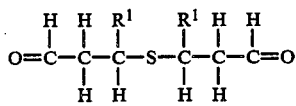　III where $R^1$ has the above meanings, and a 3-formyl-4-hydroxytetrahydrothiopyran of the formula

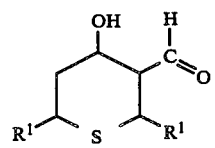　IV where $R^1$ has the above meanings, is converted in the presence of an acidic catalyst, and then, in a third stage, the resulting 3-formyl-5,6-dihydro-2H-thiopyran of the formula

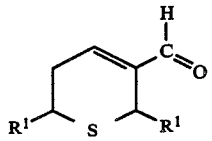　II where $R^1$ has the above meanings, is hydrogenated in the presence of a catalyst containing nickel, cobalt, platinum, copper and/or silver.

We have furthermore found that the process can advantageously be carried out if the hydrogenation catalyst used is a catalyst which contains nickel, cobalt, platinum, copper and/or silver and additionally contains basic oxides.

Where acrolein is used in the three-stage procedure according to the invention, the reactions can be represented by the following equations:

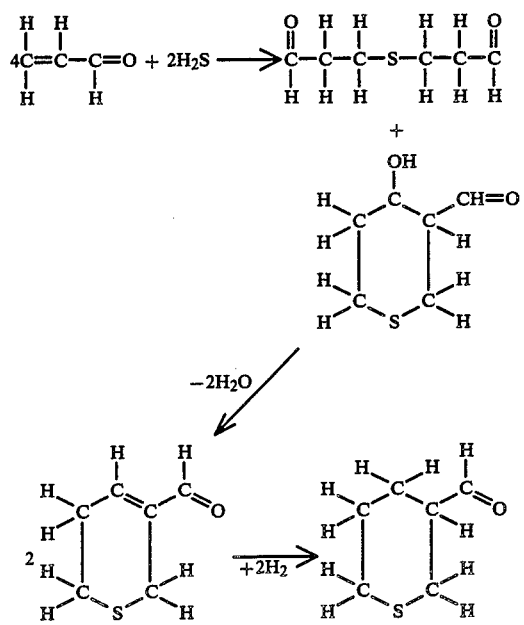

Compared with the conventional processes, the process according to the invention gives 3-formyltetrahydrothiopyrans by a simpler and more economical route and in better yield and purity. In view of the prior art, all these advantageous results are surprising. For example, it was not to be expected that, in the hydrogenation of 3-formyl-5,6-dihydro-2H-thiopyrans, palladium catalysts would rapidly be poisoned (Comparative Example 5), whereas the novel catalysts, in particular nickel catalysts, effect very selective hydrogenation and can be employed repeatedly without any significant loss of activity. According to Hartough (loc. cit.), it was to be presumed that rapid poisoning of the novel nickel catalysts would take place. With regard to German Laid-Open Application DOS 2,832,699 and the publication by Freifelder (loc.cit.), it was particularly surprising that no substantial perhydrogenation of the thiopyrans to the corresponding alcohols takes place. In any case, in view of this publication, the work of Hartough (loc.-cit.) and the article in Angew. Makromol. Chem. (loc.-cit.), a substantial decrease in the activity of the catalyst, the cleavage of the thiopyran ring, and the formation of hydrogen sulfide and of heterogeneous mixtures of a large number of cleavage products and byproducts were to be expected.

The reaction of acroleins with hydrogen sulfide to give a mixture of bis-(β-formylethyl)sulfides III and 3-formyl-4-hydroxytetrahydrothiopyrans IV in the presence of a tertiary amine can also be carried out by initially taking the acrolein and feeding in the hydrogen sulfide or, more advantageously, feeding acrolein and hydrogen sulfide simultaneously into the reaction space, under atmospheric pressure and at between 10° and 60° C.; this procedure is surprising in view of German Published Application DAS 1,919,504. It is also impossible to deduce from this publication that, in the novel process, methylene chloride, aromatic hydrocarbons and, preferably, 1,1,2-trichloroethane can be used as solvents whereas alcohols give poorer results, and, surprisingly, 1,1,1-trichloroethane, in contrast to the isomer compound 1,1,2-trichloroethane, does not give any substantial amount of starting materials III and IV, but only undesirable polymeric products (Comparative Experiment 2).

The reaction (hydrogenation) can be carried out using a stoichiometric amount or an excess of hydrogen, advantageously from 1 to 50, in particular from 1 to 10, moles of hydrogen per mole of starting material II. Preferred starting materials II and compounds III, IV and V, and accordingly preferred end products I, are those in whose formulae the individual radicals $R^1$ are each hydrogen or alkyl of 1 to 8, in particular 1 to 4, carbon atoms. The abovementioned radicals can be further substituted by groups which are inert under the reaction conditions, eg. alkyl of 1 to 4 carbon atoms.

For example, the following thiopyrans can be used as starting materials II: 2-methyl-, 2-ethyl-, 2-propyl-, 2-isopropyl-, 2-butyl-, 2-isobutyl-, 2-sec.-butyl- and 2-tert.-butyl-3-formyl-5,6-dihydro-2H-thiopyran; 3-formyl-5,6-dihydro-2H-thiopyrans which are substituted by the above groups in the 6-position instead of the 2-position; and 3-formyl-5,6-dihydro-2H-thiopyrans which are disubstituted in the 2- and 6-positions by the above groups. 3-Formyl-5,6-dihydro-2H-thiopyran is preferred.

The reaction (hydrogenation) is carried out as a rule at from 10° to 180° C., preferably from 50° to 150° C., under atmospheric or reduced pressure, but preferably under superatmospheric pressure, expediently under between 1 and 300, advantageously between 1 and 205, preferably between 1 and 155, very preferably between 1 and 100, in particular from 5 to 50, bar, either continuously or batchwise. Advantageously, organic solvents which are inert under the reaction conditions are used. Examples of suitable solvents are ethers, eg. ethyl propyl ether, methyl tert.-butyl ether, n-butyl ethyl ether, di-n-butyl ether, diisobutyl ether, diisopropyl ether, diethyl ether, diethylene glycol dimethyl ether, tetrahydrofuran or dioxane, alkanols and cycloalkanols, such as ethanol, methanol, n-butanol, isobutanol, tert.-butanol, glycol, 3-methoxypropanol, sec.-butanol, n-propanol, isopropanol, cyclohexanol, ethylene glycol monoethyl ether, 2-ethylhexanol, methylglycol, n-hexanol, isohexyl alcohol, isoheptyl alcohol, n-heptanol, ethylbutanol, nonyl alcohol, dodecyl alcohol or methyl cyclohexanol, in particular those of 1 to 4 carbon atoms, tertiary amines, such as N-methylpiperidine or N-methylmorpholine, carboxamides, such as N,N-dimethylbenzamide, N,N-dimethylformamide, N,N-dimethylacetamide, N,N-dimethylphenylacetamide, N,N-dimethylcyclohexanecarboxamide, N,N-dimethylpropionamide and homologous N-methylcarboxylic acid piperidides and N-methylcarboxylic acid pyrrolidides, the corresponding N,N-diethyl, N,N-dipropyl, N,N-diisopropyl, N,N-diisobutyl, N,N-dibenzyl, N,N-diphenyl, N-methyl-N-phenyl, N-cyclohexyl-N-methyl and N-ethyl-N-tert.-butyl compounds, N-methylformanilide, N-ethylpiperid-6-one, N-methylpyrrolidone and tetramethylurea, and preferably esters, such as methyl acetate, ethyl acetate, n-propyl acetate, isobutyl formate, methyl propionate, n-butyl acetate, ethyl formate, methyl phthalate, methyl benzoate or phenyl acetate, and appropriate mixtures. Advantageously, the solvent is used in an amount of from 10 to 10,000, preferably from 10 to 1,000, % by weight, based on starting material II.

The following metals are used for the preparation of the catalysts for the hydrogenation by the process according to the invention: nickel, cobalt, platinum, copper and silver. The catalysts can be used without a carrier, eg. Raney nickel or Raney cobalt, or in the form of supported catalysts. The catalysts without a carrier may furthermore be compounds of the metals according to the invention, preferably their oxides. Examples of suitable carriers are carbon, silica gel, aluminum silicate or alumina. Such supported catalysts can be prepared in any desired manner, for example by impregnating the carrier with appropriate solutions of metal salts, or by kneading or mixing with milling of the components. Regarding details of the preparation of catalysts, in particular supported catalysts, reference may be made to Houben-Weyl, Methoden der Organischen Chemie, Volume 4/2, page 137 et. seq. In the supported catalysts, the metal content is usually from 0.05 to 19.5, preferably from 0.5 to 15, % by weight, based on the weight of the carrier. The metal according to the invention (Ni, Co, Cu, Pt or Ag) in the hydrogenation catalyst is used as a rule in an amount of from 0.1 to 100, in particular from 0.5 to 20, % by weight, based on starting material II.

In a preferred embodiment, the catalysts contain, in addition to the metals or metal compounds according to the invention, basic oxides, as a rule basic oxides of metals of groups IIa and IIIa of the periodic table, advantageously oxides of calcium, of magnesium and/or of the rare earth metals, in particular of praseodymium or cerium. The arrangement of these groups is based on D'Ans-Lax, Taschenbuch fur Chemiker und Physiker (Springer, Berlin, 1967), Volume 1, page 63. The content of basic metal oxides in the catalyst is advantageously between 0.5 and 90, preferably from 0.5 to 30, % by weight, based on the catalyst or on the supported catalyst, and the basic metal oxide, eg. magnesium oxide, can itself constitute the carrier or a part thereof.

In the continuous or batchwise procedure, the catalyst or supported catalyst is advantageously used in the form of extrudates or of a powder.

The reaction can be carried out as follows. A mixture of starting material II, hydrogen, the catalyst and, if required, a solvent is reacted at the reaction temperature and under the reaction pressure. The hydrogen can be fed continuously or batchwise to the reaction and/or the catalyst itself can be recharged with a fresh amount of hydrogen after a certain reaction time. As a rule, hydrogen is fed to the reaction mixture at the beginning and in the course of the reaction, in amounts such that, at the reaction temperature, an appropriate reaction pressure is always maintained. In order to establish an appropriate pressure, it is also possible to use inert gases, such as nitrogen, in addition to hydrogen. For example, the starting material II and the solvent are introduced into the reactor, the hydrogenation catalyst is added, and the reaction space is flushed with nitrogen. Hydrogen is then forced in until the abovementioned reaction pressure is reached, after which the reaction mixture is brought to the abovementioned temperature and, while continuing the passage of hydrogen, is kept at this temperature until hydrogen is no longer consumed as a result of the reaction. The reaction mixture is then cooled and filtered, and the end product is isolated from the filtrate by a conventional method, for example by distillation.

The starting material II can be prepared in any desired manner, for example by the methods described in German Published Application DAS 1,919,504. In two preferred embodiments, an acrolein V is reacted with hydrogen sulfide, this being done in embodiment a in the presence of a basic catalyst together with the solvent methylene chloride, aromatic hydrocarbons and/or, preferably, 1,1,2-trichloroethane, and in embodiment b in the presence of a carboxamide which simultaneously acts as a basis catalyst and as a solvent. Both procedure a and procedure b are advantageously carried out at from $-15°$ to $+60°$ C., preferably from $-8°$ to $+40°$ C., under atmospheric, superatmospheric or reduced pressure, either continuously or batchwise. The solvents stated for procedure a or b are used individually or in the form of an appropriate mixture. Advantageously, the solvent or the solvent mixture is used in an amount of from 10 to 10,000, preferably from 10 to 1,000, % by weight, based on starting material V. Starting material V and hydrogen sulfide can be reacted in stoichiometric amounts or using either component in excess; advantageously, from 0.3 to 10, preferably from 0.5 to 2, moles of hydrogen sulfide are employed per mole of acrolein V.

The reaction in procedure (a) is carried out in the presence of a basic compound as a catalyst, this compound advantageously being used in an amount of from 0.001 to 0.1, preferably from 0.005 to 0.05, equivalent per mole of starting material V. Preferred basic compounds are tertiary amines, but it is also possible to use alkaline earth metal compounds, ammonium compounds, alkali metal compounds or primary or secondary amines. Examples of suitable basic compounds are potassium hydroxide, sodium hydroxide, potassium carbonate, sodium carbonate, sodium bicarbonate, potassium bicarbonate, calcium hydroxide, calcium oxide, barium oxide, magnesium hydroxide, magnesium oxide, barium hydroxide, calcium carbonate, sodium formate, sodium acetate, potassium formate, potassium acetate, sodium methylate, sodium ethylate, potassium methylate, potassium ethylate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, dimethylamine, diethylamine, dipropylamine, diisopropylamine, dibutylamine, diisobutylamine, pyrrolidone, piperidine, pyrrolidine, imidazole, pyrrole, N,N'-dimethylethylenediamine, N,N'-diethylethylenediamine, morpholine, hexamethyleneimine, methylamine, ethylamine, propylamine, isopropylamine, butylamine, sec.-butylamine, tert.-butylamine, anilne, N-methylpyrrolidone, N-ethylpyrrolidone, N-methylpiperidine, N-ethylpiperidine, N-methylpyrrolidine, N-ethylpyrrolidine, N-ethylpyrrole, N-methylmorpholine, N-ethylmorpholine, N-methylhexamethyleneimine, N-ethylhexamethyleneimine, pyridine, quinoline and pyrimidine.

In procedure (b), the carboxamides are employed individually or as a mixture, advantageously in the absence of an additional solvent. If required, they can also be used together with aromatic hydrocarbons, 1,1,2-trichloroethane and/or methylene chloride, advantageously in the ratio (based on acrolein V) already stated for procedure (a), or together with the basic catalysts and one solvent or the two solvents of procedure (a), advantageously under the abovementioned reaction conditions for (a). Suitable carboxamides are aromatic, araliphatic, cycloaliphatic or, in particular aliphatic or cyclic carboxamides, or carboxamides which are unsubstituted, monosubstituted or, preferably, disubstituted at the nitrogen atom. Preferred amides are those of the formula

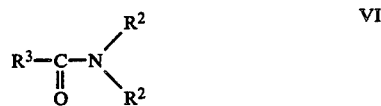

where the individual radicals $R^2$ and $R^3$ are identical or different and are each hydrogen, alkyl of 1 to 4 carbon atoms, cyclohexyl, aralkyl of 7 to 12 carbon atoms or phenyl, and $R^2$ and $R^3$ together with the adjacent carbon atom and nitrogen atom may furthermore be members of a 5-membered or 6-membered heterocyclic ring, or the radicals $R^2$ and the nitrogen atom adjacent to these two radicals may be members of a 5-membered or 6-membered heterocyclic ring, and $R^3$ may furthermore be a radical

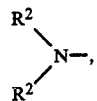

where the radicals $R^2$ have the above meanings. The radicals and rings can be further substituted by groups which are inert under the reaction conditions, eg. alkyl of 1 to 3 carbon atoms.

Examples of suitable amides are N,N-dimethylbenzamide, N,N-dimethylbutyramide, N,N-dimethylphenylacetamide, N,N-dimethylcyclohexanecarboxamide, N,N-dimethylpropionamide and homologous carboxylic acid piperidides and carboxylic acid pyrrolidides; the corresponding N,N-diethyl, N,N-dipropyl, N,N-diisopropyl, N,N-diisobutyl, N,N-dibenzyl, N,N-diphenyl, N-methyl-N-phenyl, N-cyclohexyl-N-methyl and N-ethyl-N-tert.butyl compounds; N-methylformanilide, N-ethylpiperid-6-one and tetramethylurea, and appropriate mixtures. Dimethylformamide, diethylformamide, dimethylacetamide, diethylacetamide and N-methylpyrrolidone are preferred.

The reaction according to (a) or (b) gives a mixture of the starting materials III and IV in a ratio of from 0.1 to 1 mole of starting material III (bis-($\beta$-formylethyl)sulfide) per mole of starting material IV (3-formyl-4-hydroxytetrahydrothiopyran); these starting materials can be isolated in a conventional manner, for example by fractional distillation, and can be fed to a second stage, ie. the acid treatment, either individually or as a mixture with one another. Advantageously, however, the reaction mixture from reaction (a) or (b) is not worked up; instead, the acid is added to this mixture, after which the reaction of the second stage is carried out. As a rule, a strong acid is used. For the purposes of the present invention, strong acids are organic or inorganic acids which are inert under the reaction conditions and have an exponent $pK_a$ of from $-7$ to $+2.16$. Regarding the definition of the acid exponent or of the $pK_a$ value, reference may be made to Ullmanns Encyklopadie der technischen Chemie, Volume 15, page 2. Examples of suitable compounds are sulfuric acid, phosphoric acid, hydrogen chloride gas, formic acid, boric acid, sulfonic acids, such as benzenesulfonic and p-toluenesulfonic acid, and trichloroacetic acid; ion exchangers, such as the acidic ion exchangers described in Houben-Weyl, Methoden der Organischen Chemie, Volume I/1, page 528 et.seq., preferably polystyrenesulfonic acid resins, phenolsulfonic acid resins and polyfluoroethylenesulfonic acid resins; and appropriate mixtures. Preferred acids are sulfuric acid, toluenesulfonic acid and phosphoric acid. The acid is advantageously used in an amount of from 0.005 to 2, preferably from 0.05 to 1, equivalents per mole of starting material V.

The reaction in the second stage is carried out as a rule at from 30° to 150° C., advantageously from 70° to 120° C., under atmospheric or superatmospheric pressure, either continuously or batchwise. Preferably, the reaction is carried out by process (a) or (b) and, if required, using methylene chloride, aromatic hydrocarbons and/or advantageously, 1,1,2-trichloroethane in the 1st stage, and the solvent is left in the mixture for the 2nd stage. The solvent can also be removed before or after the addition of the acid, and an additional solvent can then be added. It is also possible to add the additional solvent to the reaction mixture obtained from the 1st stage, without separating off the solvent from that stage. Suitable additional solvents, where these are required, are organic solvents which are inert under the reaction conditions, such as aromatic hydrocarbons, eg. toluene, xylene, chlorobenzene, fluorobenzene, bromobenzene or o-, p- or m-dichlorobenzene, or an appropriate mixture; advantageously, the solvent is used in an amount of from 100 to 10,000% by weight, based on the starting materials III and IV.

The reaction can be carried out as follows. A mixture of starting material V, the solvent and, if required, a base is kept at the reaction temperature. The acid is then added, if required the solvent from the 1st stage is replaced by another one for the 2nd stage, and the reaction in the 2nd stage is carried out in the mixture, which is generally a two-phase one; the starting materials III, IV and II are predominantly present in the organic phase, while the aqueous phase contains the acidic catalyst. The starting material II is then isolated in a conventional manner, for example by separating off the organic phase, extracting the aqueous phase and subjecting the combined organic phases to fractional distillation, and is employed for the hydrogenation according to the invention in the 3rd stage, in the above manner. The aqueous phase which contains the acidic catalyst can be separated off when the reaction is complete, and reused for the next batch.

In another embodiment, starting materials III and/or IV prepared by another route can also be subjected to the 2nd stage (acid treatment) in the above manner, and the resulting starting material II can be hydrogenated in the manner described above.

The compounds obtainable by the process according to the invention are useful starting materials for the preparation of dyes, drugs and pesticides, for example the herbicides described in European Patent Application 0 071 707. Regarding the use of these compounds, reference may be made to the abovementioned publications.

EXAMPLE 1

(a) Preparation of 3-formyl-5,6-dihydro-2H-thiopyran

A mixture of 2,000 ml of 1,1,2-trichloroethane and 1.3 ml of pyridine was saturated with hydrogen sulfide at 21° C. 507 g of acrolein were then added dropwise while hydrogen sulfide was passed in simultaneously, the temperature being kept at 35° C. by cooling. Hydrogen sulfide was then passed into the resulting mixture until the latter was saturated, a total of 365 g of hydrogen sulfide being taken up. A further 507 g of acrolein were then added dropwise at 32° C., without the introduction of hydrogen sulfide, and the resulting solution was stirred for a further 12 hours at 22° C., after which 1,000 ml of 37% strength by weight phosphoric acid were added to the reaction mixture. The mixture was stirred for 7 hours at 85° C. and then cooled, the organic phase was separated off, the aqueous phase was extracted with twice 500 ml of 1,1,2-trichloroethane, the combined organic phases were dried over sodium sulfate, the solvent was removed under reduced pressure, and the remaining residue was distilled under reduced pressure in a thin-film evaporator to effect separation from high boiling by-products; the resulting 1,060 g of 3-formyl-5,6-dihydro-2H-thiopyran of boiling point 75°–78° C./0.25 mbar and melting point 31° C. were employed directly in the hydrogenation.

(b) Preparation of 3-formyltetrahydrothiopyran 1,792 g of 3-formyldihydro-2H-thiopyran prepared as described in Example 1(a), 200 ml of ethyl acetate and 220 g of Raney nickel were introduced into a rotating autoclave having a capacity of 3,000 ml. The autoclave was closed, and flushed with nitrogen, after which hydrogen was forced in until the total pressure reached 20 bar, and the mixture was heated to 90° C. and hydrogenated under these conditions with further introduction of hydrogen until the pressure remained constant. The mixture was then cooled, the catalyst was filtered off and the filtrate was purified by distillation under reduced pressure. 1,658 g (91% of theory) of 3-formyltetrahydrothiopyran of boiling point 94°–95° C./10 mbar were obtained. The catalyst was employed in seventeen successive reactions 1(b) without loss of activity and with the same yield of pure end product.

EXAMPLE 2

(a) The reaction was carried out by a method similar to that described in Example 1(a), except that methylene chloride was used as a solvent, which was distilled off after the aqueous phosphoric acid had been added, and was replaced by the same amount of toluene. The reaction was then continued in an acidic medium, similarly to Example 1(a). 974 g of 3-formyl-5,6-dihydro-2H-thiopyran of boiling point 75°–78° C./0.25 mbar and melting point 31° C. were obtained.

(b) Using the starting material II obtained in this manner, the hydrogenation was carried out by a method similar to that described in Example 1(b). The results and the activity of the catalyst were the same as in Example 1(b).

EXAMPLE 3 (COMPARISON)

(a) The reaction was carried out by a method similar to that described in Example 1(a), except that 1,1,1-trichloroethane was used as the solvent. When acrolein was added dropwise, a highly exothermic reaction took place, in contrast to Example 1(a), to form white greasy polymeric products, which did not dissolve. When the reaction mixture was worked up, only rubber-like high molecular weight products were obtained.

(b) It was therefore impossible to carry out a reaction similar to that described in Example 1(b).

EXAMPLE 4

A mixture comprising 32 g of 3-formyl-5,6-dihydro-2H-thiopyran, 100 ml of ethyl acetate and 3.2 g of a catalyst (composition: 7.9% by weight of nickel, 7.9% by weight of cobalt and 3.2% by weight of copper on alumina) was introduced into a stirred autoclave having a capacity of 300 ml. The mixture was then hydrogenated at 140° C. and under a hydrogen pressure of 20 bar, until the pressure remained constant. 28 g (86% of theory) of 3-formyltetrahydrothiopyran were isolated by distillation under reduced pressure. The catalyst was reused in 17 further reactions without any deterioration in the results.

EXAMPLE 5

The reaction was carried out by a method similar to that described in Example 4, except that 3.2 g of Raney cobalt were used as the catalyst, and the hydrogenation temperature was 120° C. Under these conditions, 3-formyltetrahydrothiopyran was obtained in a yield of 88% of theory. The catalyst are reused in 17 further reactions without any deterioration in the results.

EXAMPLE 6 (COMPARISON)

The reaction was carried out by a method similar to that described in Example 4, using 3.2 g of a catalyst containing 10% by weight of palladium on active carbon. 25 g of reaction product were obtained which had the following composition according to analysis by gas chromatography:

7% of 3-methyltetrahydrothiopyran,
86% of 3-formyltetrahydrothiopyran and
7% of 3-formyl-5,6-dihydro-2H-thiopyran.

The catalyst was employed in the reaction a second time, and a substantial loss of activity was found; the yield was only 12% of theory.

EXAMPLE 7

A mixture comprising 38.4 g of 3-formyl-5,6-dihydro-2H-thiopyran, 100 g of methanol and 6.5 g of a catalyst (composition: 5% by weight of platinum, 2.5% by weight of praseodymium oxide on alumina) was introduced into a stirred autoclave having a capacity of 300 ml. The mixture was then hydrogenated at 130° C. and under a hydrogen pressure of 50 bar until the pressure remained constant. 37 g of reaction product were obtained which had the following composition according to analysis by gas chromatography:

3% of 3-methyltetrahydrothiopyran,
92% (87% of theory) of 3-formyltetrahydrothiopyran and
5% of 3-formyl-5,6-dihydro-2H-thiopyran.

The catalyst was reused in 17 further reactions without any deterioration in the results.

EXAMPLE 8

A procedure similar to that described in Example 7 was employed, except that 6.5 g of a catalyst composed of 5% by weight of platinum and 1% by weight of silver on alumina were used. The solvent employed was tetrahydrofuran. The reaction product obtained under these conditions had the following composition according to analysis by gas chromatography:

88% (83.6% of theory) of 3-formyltetrahydrothiopyran,
3% of 3-formyl-5,6-dihydro-2H-thiopyran and
9% of 3-hydroxymethyltetrahydrothiopyran.

The catalyst was reused in 17 further reactions without any deterioration in the results.

EXAMPLE 9

A procedure similar to that described in Example 7 was employed, except that 6.5 g of a catalyst composed of 5% by weight of platinum on a carrier consisting of 19.4% by weight of magnesium oxide and 80.6% by weight of alumina were used. Under these conditions, the following results were obtained, according to analysis by gas chromatography:

5% of 3-methyltetrahydrothiopyran,
91% (86.5% of theory) of 3-formyltetrahydrothiopyran,
1% of 3-formyl-5,6-dihydro-2H-thiopyran and
3% of 3-hydroxymethyltetrahydrothiopyran.

The catalyst are reused in 17 further reactions without any deterioration in the results.

EXAMPLE 10

(a) 130 g of hydrogen sulfide were passed into a solution of 420 g of acrolein and 42 g of dimethylformamide at −5° C. in the course of 3 hours, an immediate reaction taking place. 600 ml of toluene and 100 ml of 75% strength by weight phosphoric acid were added to the resulting reaction mixture at 20° C., and the mixture was heated at 115° C. for 2 hours while water was separated off at the same time. When 65 ml of water had been separated off, the mixture was distilled to give 430 g (89% of theory) of 3-formyl-5,6-dihydro-2H-thiopyran.

(b) The starting material II thus obtained was used to carry out the reaction similarly to Example 1(b). 1,658 parts by weight (91% of theory) of 3-formyltetrahydrothiopyran of boiling point 94°–95° C./10 mbar were obtained. The catalyst was employed in 17 successive reactions without any loss of activity and with the same yields of pure end product.

EXAMPLE 11

(a) Preparation of 3-formyl-5,6-dihydro-2,6-dimethyl-2H-thiopyran 17 g of hydrogen sulfide were passed into a mixture of 500 ml of toluene, 70 g of crotonaldehyde and 10 ml of triethylamine at 30° C. and the mixture was then stirred for 12 hours at room temperature, after which 300 ml of 37% strength by weight phosphoric acid were added. Stirring was continued for 8 hours at 90° C., after which the mixture was cooled to room temperature and the organic phase was separated off. The aqueous phase was extracted once with toluene, the combined organic phases were washed once with water and dried over sodium sulfate, the solvent was removed under reduced pressure and the residue was distilled under 0.6 mbar to give 64 g (82% of theory) of 3-formyl-5,6-dihydro-2,6-dimethyl-2H-thiopyran of boiling point 73°–76° C.

(b) Preparation of 3-formyl-2,6-dimethyltetrahydrothiopyran 100 g of 3-formyl-5,6-dihydro-2,6-dimethyl-2H-thiopyran prepared as described in Example 11(a), 60 ml of ethyl acetate and 30 g of Raney nickel were introduced into a stirred autoclave having a capacity of 300 ml. The autoclave was closed, and flushed with nitrogen. Hydrogen was forced in until the total pressure reached 30 bar, after which the mixture was heated to 90° C. and hydrogenated under these conditions until the pressure remained constant. It was then cooled, the catalyst was filtered off and the filtrate was purified by distillation under reduced pressure. 89 g (88% of theory) of 3-formyl-2,6-dimethyltetrahydrothiopyran of boiling point 127°–129° C./10 mbar were obtained.

EXAMPLE 12

(a) The preparation of 3-formyl-5,6-dihydro-2H-thiopyrans was carried out by a method similar to that described in Example 1a.

(b) Preparation of 3-formyltetrahydrothiopyran 1,792 g of 3-formyldihydro-2H-thiopyran prepared as described in Example 1(a, 200 ml of N,N-dimethylformamide and 75 g of Raney nickel were introduced into a stirred autoclave having a capacity of 3,000 ml. The autoclave was closed, and flushed with nitrogen. Hydrogen was then forced in until the total pressure reached 200 bar, and the mixture was heated to 130° C. and, while continuing the introduction of hydrogen, was hydrogenated under these conditions until the pressure remained constant. The mixture was then cooled, the catalyst was filtered off and the filtrate was purified by distillation under reduced pressure. 1639 g (90% of theory) of 3-formyl-tetrahydrothiopyran of boiling point 94°–95° C./10 mbar were obtained.

EXAMPLE 13

(a) The preparation of the starting material II and (b) the hydrogenation were carried out similarly to Example 12, a pressure of 150 bar being employed for the hydrogenation. 1676 g (92% of theory) of 3-formyltetrahydrothiopyran of boiling point 94°–95° C./10 mbar were obtained.

We claim:

1. A process for the preparation of a 3-formyltetrahydrothiopyran of the formula

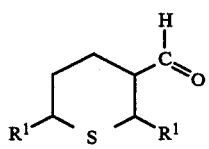

I where the individual radicals $R^1$ are each hydrogen or an aliphatic radical, which comprises: hydrogenating a 3-formyl-5,6-dihydro-2H-thiopyran of the formula

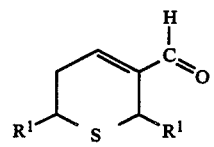

II where $R^1$ has the above meanings, in the presence of a catalyst containing nickel, cobalt, platinum, copper and/or silver.

2. A process as claimed in claim 1, wherein, in a first stage, a bis-(-formylethyl)sulfide of the formula

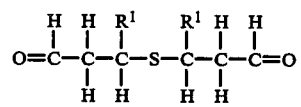

III where $R^1$ has the above meanings, and/or a 3-formyl-4-hydroxytetrahydrothiopyran of the formula

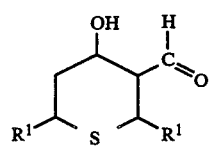

IV where $R^1$ has the above meanings, are converted in the presence of an acidic catalyst, and then, in a second stage, the resulting 3-formyl-5,6-dihydro-2H-thiopyran of the formula

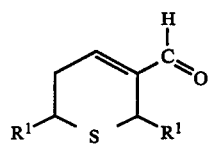

II where $R^1$ has the above meanings, is hydrogenated in the presence of a catalyst containing nickel, cobalt, platinum, copper and/or silver.

3. A process as claimed in claim 1, wherein, in a first stage, an acrolein of the formula

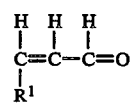

V where $R^1$ has the above meanings, is reacted with hydrogen sulfide (a) in the presence of a basic catalyst and of methylene chloride, an aromatic hydrocarbon and/or 1,1,2-trichloroethane as the solvent and/or (b) in the presence of a carboxamide, and then, in a second stage, the resulting mixture of a bis-(β-formylethyl)sulfide of the formula

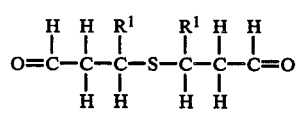

III where $R^1$ has the above meanings, and a 3-formyl-4-hydroxytetrahydrothiopyran of the formula

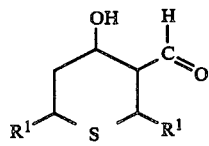

where R¹ has the above meanings, is converted in the presence of an acidic catalyst, and then, in a third stage, the resulting 3-formyl-5,6-dihydro-2H-thiopyran of the formula

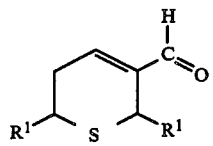

where R¹ has the above meanings, is hydrogenated in the presence of a catalyst containing nickel, cobalt, platinum, copper and/or silver.

4. A process as claimed in claim 1, wherein the hydrogenation catalyst used is a catalyst which contains nickel, cobalt, platinum, copper and/or silver and additionally contains basic oxides.

5. A process as claimed in claim 1, wherein the hydrogenation is carried out using from 1 to 50 moles of hydrogen per mole of starting material II.

6. A process as claimed in claim 1, wherein the hydrogenation is carried out at from 10° to 180° C.

7. A process as claimed in claim 1, wherein the hydrogenation is carried out at from 50° to 150° C.

8. A process as claimed in claim 1, wherein the hydrogenation is carried out under a pressure of between 1 and 300 bar.

9. A process as claimed in claim 1, wherein the hydrogenation is carried out under a pressure of between 1 and 205 bar.

10. A process as claimed in claim 1, wherein the hydrogenation is carried out under a pressure of between 1 and 155 bar.

11. A process as claimed in claim 1, wherein the hydrogenation is carried out under a pressure of between 1 and 100 bar.

12. A process as claimed in claim 1, wherein the hydrogenation is carried out in the presence of an organic solvent.

13. A process as claimed in claim 1, wherein the hydrogenation is carried out using a hydrogenation catalyst which contains from 0.1 to 100% by weight, based on starting material II, of metal.

14. A process as claimed in claim 1, wherein the hydrogenation is carried out using a catalyst which contains between 0.5 and 90% by weight, based on the catalyst or on the supported catalyst, of basic metal oxides.

15. A process as claimed in claim 3, wherein the reaction in the 1st stage is carried out at from −15° to +60° C.

16. A process as claimed in claim 3, wherein the reaction in the 1st stage is carried out using from 0.3 to 10 moles of hydrogen sulfide per mole of acrolein V.

17. A process as claimed in claim 3, wherein the reaction in the 1st stage is carried out using from 0.001 to 0.1 equivalent of a basic compound per mole of starting material V.

18. A process as claimed in claim 3, wherein the reaction in the 2nd stage is carried out at from 30° to 150° C.

19. A process as claimed in claim 1, wherein the catalyst is selected from the group consisting of Raney nickel and Raney cobalt catalysts.

20. A process as claimed in claim 1, wherein the hydrogenation is carried out using a catalyst which contains from 0.6 to 20% by weight, based on starting material II, of metal.

* * * * *